Figure 1A:
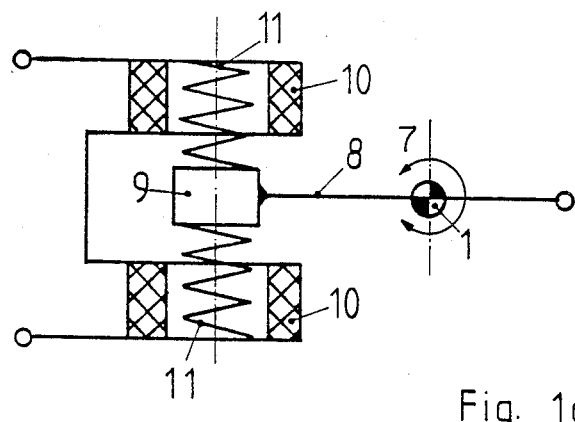

United States Patent [19]

Reis et al.

[11] Patent Number: 4,850,687
[45] Date of Patent: Jul. 25, 1989

[54] DEVICE FOR MOVING A BEAM OF LIGHT IN A PLANE OF IMPACT

[75] Inventors: Werner Reis, Munich; Siegfried Cierlak, Bad Wiessee, both of Fed. Rep. of Germany

[73] Assignee: G. Rodenstock Instrumente GmbH, Munich, Fed. Rep. of Germany

[21] Appl. No.: 146,810

[22] PCT Filed: Apr. 18, 1987

[86] PCT No.: PCT/DE87/00177
§ 371 Date: Feb. 18, 1988
§ 102(e) Date: Feb. 18, 1988

[87] PCT Pub. No.: WO87/06358
PCT Pub. Date: Oct. 22, 1987

[30] Foreign Application Priority Data

Apr. 18, 1986 [DE] Fed. Rep. of Germany ....... 3613233

[51] Int. Cl.$^4$ ............................................. G02B 26/08
[52] U.S. Cl. ..................................... 350/486; 350/632
[58] Field of Search ................ 350/486, 484, 500, 6.9, 350/6.91, 632, 633, 634, 635, 636, 637, DIG. 3

[56] References Cited

U.S. PATENT DOCUMENTS

| | | | |
|---|---|---|---|
| 4,057,331 | 11/1977 | Ong et al. | 350/486 |
| 4,157,861 | 6/1979 | Davies | 350/486 |
| 4,175,832 | 11/1979 | Umeki et al. | 350/486 |
| 4,269,486 | 5/1981 | Shintahi | 350/6.5 |
| 4,500,867 | 2/1985 | Ishitobi | 338/128 |
| 4,573,467 | 3/1986 | Rich et al. | 128/303.1 |
| 4,626,063 | 12/1986 | Honey | 350/6.9 |
| 4,680,522 | 7/1987 | St. Clair et al. | 350/486 |
| 4,714,214 | 12/1987 | Schleimann-Jensen et al. | 74/5.7 |
| 4,738,500 | 4/1988 | Grupp et al. | 350/486 |

FOREIGN PATENT DOCUMENTS

WO85/00966 3/1985 PCT Int'l Appl. .

Primary Examiner—Bruce Y. Arnold
Assistant Examiner—Ronald M. Kachmarik
Attorney, Agent, or Firm—Antonelli, Terry & Wands

[57] ABSTRACT

A device for steady-state adjustment of a light beam enabling laser treatment in an impact plane including a joint enabling rotational movement about one axis and tilting movement about another axis extending perpendicularly to the one axis. The joint is biased to a predetermined position and a mirror is mounted on the joint with first and second magnet-coil arrangments being separately mounted on the joint for respectively enabling independent tilting movement of the joint and the mirror about the one axis and independent rotational movement of the joint and the mirror about another axis. A control unit is provided for controlling current flow in coils of the first and second magnet-coil arrangements to effect movement of the joint and the mirror, whereby the mirror is adjusted to enable deflection of light beam to an impact point in the impact plane.

11 Claims, 2 Drawing Sheets

DEVICE FOR MOVING A BEAM OF LIGHT IN A PLANE OF IMPACT

BACKGROUND OF THE INVENTION

The present invention relates to a device for moving a beam of light in a plane of impact.

STATE OF THE ART

Devices of this type are needed, by way of illustration, in so-called laser coagulators such as are employed in ophthalmology. Furthermore, there are, of course, numerous other possible applications in various fields of technology for such devices, for example, in laser welding.

A device as described herein is, for example, the so-called "micromanipulator" developed by the present applicant. In said prior art device, a mirror deflecting the laser beam toward the eye, is moved pneumatically. Said mirror may, for example, be one of the mirrors deflecting the operation and/or target beam in the device described in WO 85/00966 or the one described in DE-GM 7 225 429.

This prior art device is—as was recognized in accordance with the present invention—not optimum in some instances due to the fact that the mirror is moved pneumatically:

The known micromanipulator cannot be readily operated and/or programmed by remote control via a suitable electronic system. The response time of the manipulator may, under circumstances, be "noticeable" during the operation. Furthermore, the manipulation operation is not always noiseless.

DESCRIPTION OF THE INVENTION

The object of the present invention is to provide a device for moving a beam of light in a plane of impact permitting quick, precise and electronically controlled manipulation of a beam in a plane of impact.

One solution of the object is successful by still proceeding from a device in which a mirror, which deflects a beam of light, is tilted or rotated. An inventive element is that said mirror is fixed to a tilting/rotating joint, which is biased, by means of a bias device, to a home position and is connected to magnets. Said magnets are in a magnetic field created by current-carrying coils. By varying the current flowing through the coils and thus the created magnetic field, it is possible to tilt the tilting/rotating joint and thereby the mirror in a defined manner. The point of impact of the light beam in the plane of impact is moved in a defined manner corresponding to the defined tilting. The invented device has a number of advantages:

The tilting of the mirror and thus the moving of the beam of light in the plane of impact occurs quickly and noiselessly. The system has a defined home position, in which, for example, the laser beam is directed exactly at the geometric center of the field, over which the laser beam may be moved. On the other hand, with a device control unit, for example, an electronic control, it is possible to convey the system into any desired home position with a constant current. In any case, however, it is possible to manipulate the light beam in the plane of impact as the biased tilting/rotating joint is supported in bearings with practically no backlash.

In accordance with the present invention, the mirror can be rotated about one axis and tilted about another axis, which are perpendicular to each other, and rotating and tilting the mirror about each of these axes ensues by means of a respective coil/magnetic unit, permits the simplest x/y-moving of the point of impact of the light beam in the plane of impact.

By means of the "symmetrically rotating" feature of the present invention, tilting moments, which might reduce the precision of the adjustment, are effectively reduced.

The circuit arrangement of the present invention increases the symmetry of the invented device and thereby reduces the danger of the occurrence of tilt moments.

By reversing the currents flowing through the coils, the mirror may be tilted or rotated in both directions even in a symmetrical arrangement.

Various possible bias devices are utilized, which bias the device to its home position.

The invented device may also be regulated by hand, by means of a control stick as well as by a control unit.

The control unit permits a programmed moving of the point of impact of the light beam or, for example, moving controlled by a image processing device. Hereby, the rapid reaction of the invented device permits making corrections in "real time", for example, during a laser shot during laser treatment of the human eye.

Naturally, simple remote control is also possible. Furthermore, the solely electrical operation and control of the invented device permits, for example, an electronic "transmission" of the movements of the control stick.

An advantageous embodiment of a control stick includes a permanent magnet arranged in a movable manner via magnetic field plates. However, other embodiments are, of course, also possible as they are employed with so-called "joy sticks", as long as they permit the translation of a shift or a movement of the stick in a plane into "homing signals" for the coils.

A further advantage of the invented device is that the "solely electronic control" of beam movement permits, for example, connecting, in a simple manner, a recorder printer or a storage unit with which the manipulation of beam can be recorded, which may be, for example, important in ophthalmology in the event of liability claims, etc.

In any case, the invented device is particularly suitable for manipulating a laser beam in an eye examination or eye treatment apparatus. For the working manner of the invented device it makes no difference whether the laser is an argon laser for retina treatment, a neodymium YAG laser for cutting in the front eye media or an excimer or 3<m-laser for keratotomy.

A BRIEF DESCRIPTION OF THE DRAWING

Figure 2:
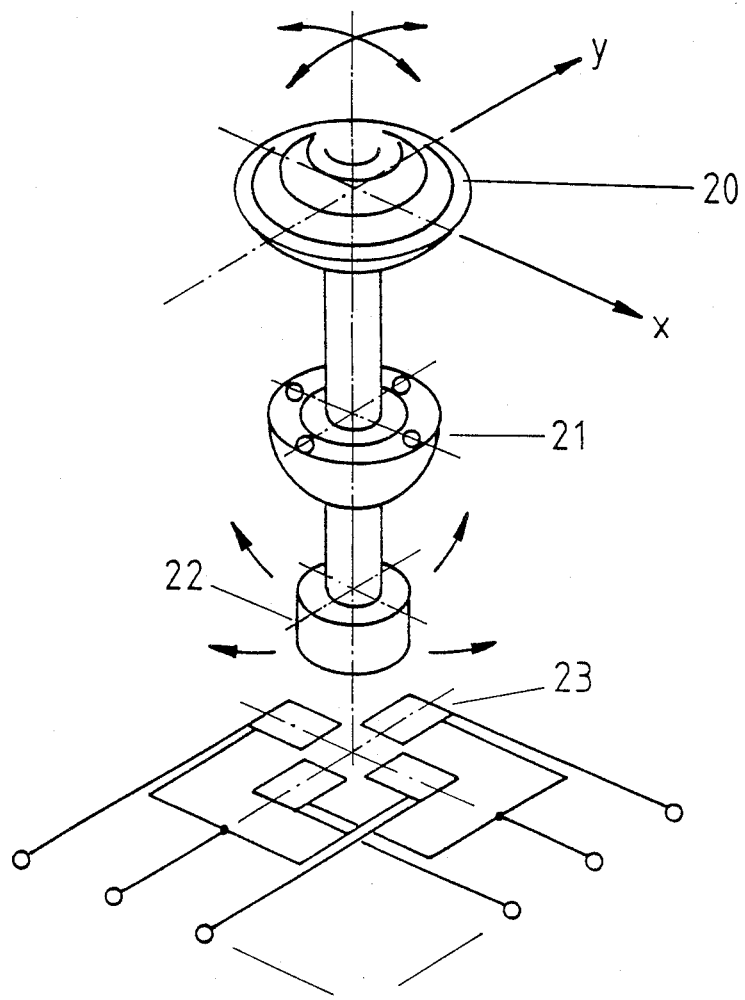

The present invention is made more apparent in the following using preferred embodiments in connection with the drawing, which expressly refers to all the details not disclosed in the text, depicting:

FIGS. 1a and b two preferred embodiments of biasing arrangements of an invented device, and FIG. 2 a preferred embodiment of a control stick.

PRESENTATION OF A PREFERRED EMBODIMENT

Figure 1B:
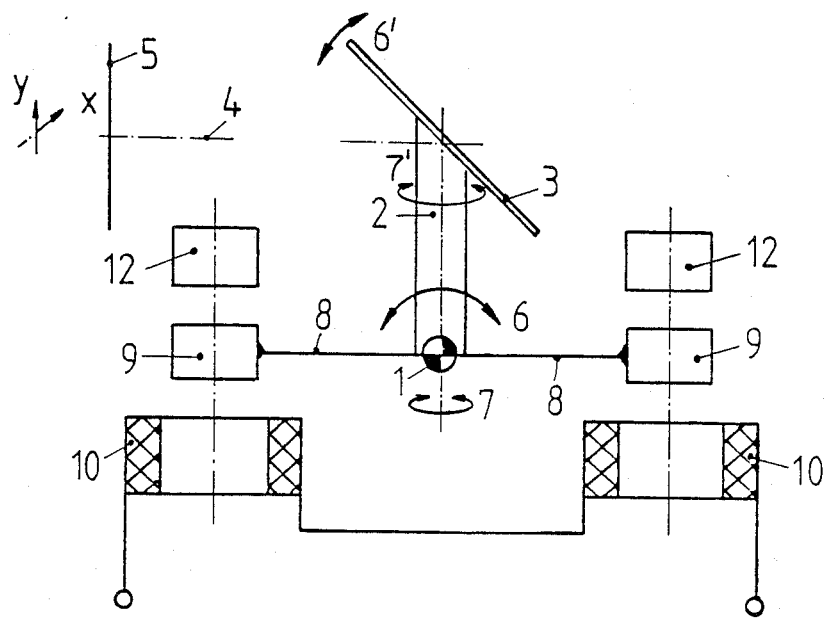

FIGS. 1a and 1b shows two preferred embodiments, which differ essentially in the construction of the bias device, which defines the home position. Both embodiments are provided with a tilting/rotating joint 1, to which two holders 2 are fixed, of which only one is depicted in the figures herein, for a mirror 3. Between both holders 2 runs a beam of light and, in particular, a laser beam 4, which is deflected by mirror 3 and whose point of impact is to be manipulated in a plane of impact 5, which is only depicted schematically. The only schematically depicted tilting/rotating joint is constructed in such a manner that it is provided with a channel of passage for the laser beam.

Joint 1 can be moved in the direction of the arrow so as to effect tilting about one axis 6 and the arrow 7 so as to effect rotational movement about another mutually perpendicular axis so that the mirror 3 moves the direction of the arrows 6' and 6' and beam 4 is moved in the plane 5 in x/y direction.

A coil/magnet unit has been provided to move the tilting/rotating joint 1 so as to effect tilting movement in the direction of arrow 6, which shall be made more apparent in the following referring to FIG. 1b. An identical unit has been provided to move joint 1 to effect rotational movement in the direction of arrow 7 referring to FIG. 1a.

To joint 1 are fixed, by means of rods 8, permanent magnets 9, which are in a B-field, created by current-carrying coils 10. Said coils 10 are each connected to another in such a manner that a flow of current generates energy in one direction attracting one of the permanent magnets 9 and repelling the other. By controlling the flow of the current and its direction, a defined tilting/rotational movement of joint 1 can be produced and thereby a defined movement of mirror 3. Furthermore, a bias device has been provided, which defines the home position of joint 1 when coils 10 are not charged and thereby the home position of mirror 3. In the preferred embodiment depicted in FIG. 1a, the bias device is composed of two springs 11 and in the preferred embodiment according to FIG. 1b of two more permanent magnets 12, which exercise an "equidirectional" force on magnets 9.

FIG. 2 shows a preferred embodiment of a control stick for the manual control of the invented device. The control stick is provided with a knob 20, a ball seat 21, which permits moving said knob in x/y-direction, and a magnet 22, which is connected to ball seat 21. Moreover, magnetic field plates 23 have been provided, for the arrangement and circuit of which the figure is to be referred to. Each pair of magnetic field plates 23 is connected to a coil configuration 10 of the invented device by means of an intermediate amplifier, which is not depicted in the figure. Moving said knob 20 in the x/y plane and the thus resulting shifting of the magnets changes the current flowing through the magnetic field plates and thus through coils 9 in proportion to the movement. The mirror is then tilted and rotated correspondingly to manipulate the beam.

In the preceeding the present invention has been described using preferred embodiments without the intention of limiting the scope of the general inventive idea as is set forth in the claims herein.

For example, it is possible to employ a device according to FIG. 1a to rotate joint 1 in one direction about a vertical axis to effect mirror and laser beam movement in the X plane and a device according to FIG. 1b to tilt it in the other direction about a horizontal axis to effect mirror and laser beam movement in the Y plane. Other control sticks constructed in a different manner may be used instead of the control stick depicted in FIG. 2.

Instead of manual control, it is also possible to use program control or automatic control, by way of illustration, an image processing device.

Furthermore, when employing a manual control, the "transmission" between the movement of the control stick and the direction of the laser beam may be changed, for example, by changing the amplification factor of the intermediate amplifier.

If necessary, the coils and the permanent magnets may be exchanged, thus the coils are arranged at joint 1 without changing the function of the invented device.

When the invented device is employed in a laser with a slit lamp apparatus, it is, for example, when guiding the beam through the microscope arm, particularly advantageous if one of the mirrors in the microscope arm is tilted by the invented device.

What I claim is:

1. A device for steady-state adjustment of a light beam enabling laser treatment in an impact plane comprising joint means enabling rotational movement about one axis and tilting movement about another axis extending perpendicularly to the one axis, biasing means for biasing the joint means to a predetermined position, a mirror mounted on the joint means, first and second magnet-coil means separately mounted on the joint means for respectively enabling tilting movement of the joint means and the mirror about the one axis and rotational movement of the joint means and the mirror about the another axis independent of each other, and control means for controlling current flow in coils of the first and second magnet-coil means to effect movement of the joint means and the mirror, whereby the mirror is adjusted to enable deflection of a light beam to an impact point in the impact plane.

2. A device according to claim 1, wherein each of said first and second magnet-coil means comprises two magnets and two associated coils disposed at opposite sides of the joint means at equal distances from the joint means.

3. A device according to claim 3, wherein the two associated coils of each of said first and second magnet-coil means are connected in series.

4. A device according to one of claims 1, 2 or 3 wherein the control means enable flow of current through the coils in reversible directions.

5. A device according to claims 1, 2 or 3, wherein the biasing means comprises springs for biasing the joint means to the predetermined position.

6. A device according to one of claims 1, 2 and 3, wherein the biasing means comprises springs associated with the first and second magnet-coil means for biasing the joint means to the predetermined position.

7. A device according to one of claims 1, 2 or 3, wherein the biasing means comprises permanent magnet means associated with the coil-magnet means for biasing the joint means to the predetermined position.

8. A device according to claim 7, wherein the control knob is movable about axes corresponding to the one and another axes so that movement of the control knob effects a corresponding displacement of the light beam in the impact plane.

9. A device according to claim 10, wherein the control means includes field plates connected with the coils of the first and second magnet-coil means, and a permanent magnet displaceably mounted with respect to the field plates, the permanent magnet being connected to the control knob, and the field plates being responsive to the movement of the permanent magnet as effected by the control knob for controlling current flow through the coils of the first and second magnet-coil means in accordance therewith.

10. A device according to one of claims 1, 2 or 3, wherein the control means includes a control knob for controlling current flow through the first and second magnet-coil means in accordance with the position thereof.

11. A device according to claim 8, wherein the control means includes field plates connected with the coils of the first and second magnet-coil means, and a permanent magnet displaceably mounted with respect to the field plates, the permanent magnet being connected to the control knob, and the field plates being responsive to the movement of the permanent magnet as effected by the control knob for controlling current flow through the coils of the first and second magnet-coil means in accordance therewith.

* * * * *